Figure 5:
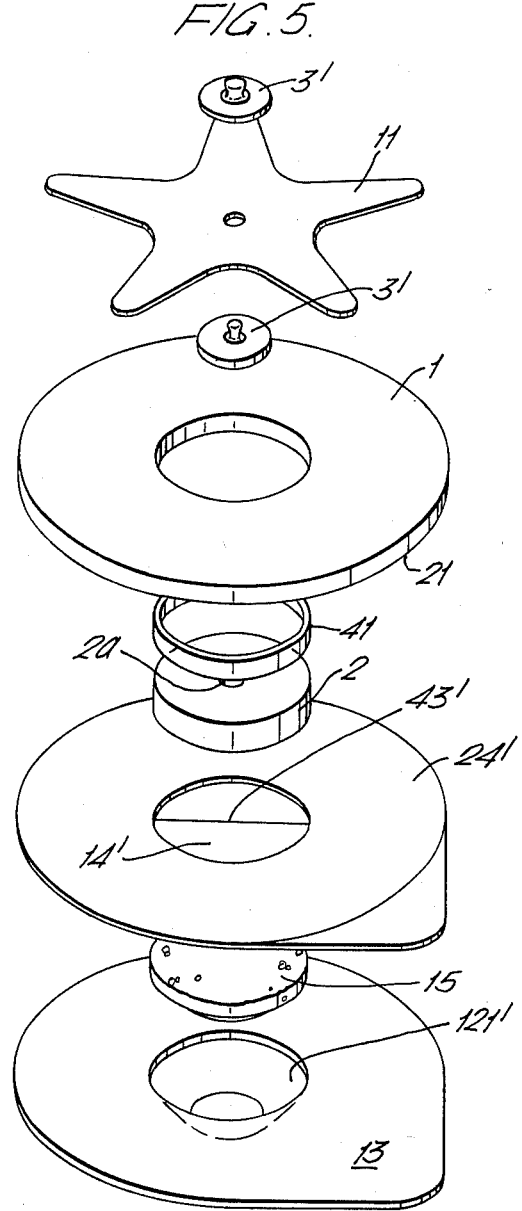

United States Patent [19]
Danby

[11] 4,079,731
[45] Mar. 21, 1978

[54] MEDICAL ELECTRODES

[75] Inventor: Hal Charles Danby, Colchester, England

[73] Assignee: Cardiolink Electrodes, Ltd., Colchester, England

[21] Appl. No.: 701,528

[22] Filed: Jul. 1, 1976

[30] Foreign Application Priority Data

Jul. 3, 1975 United Kingdom .............. 28041/75
Aug. 27, 1975 United Kingdom .............. 35283/75
Sep. 12, 1975 United Kingdom .............. 37524/75
Oct. 28, 1975 United Kingdom .............. 44251/75

[51] Int. Cl.² .............................................. A61B 5/04
[52] U.S. Cl. .............. 128/2.06 E; 128/2.1 E; 128/417; 128/DIG. 4
[58] Field of Search ............ 128/2.06 E, 2.1 E, 172.1, 128/404, 410, 411, 416–418, 260, 261, 268

[56] References Cited

U.S. PATENT DOCUMENTS

| 3,187,745 | 6/1965 | Baum et al. | 128/2.06 E |
| 3,306,292 | 2/1967 | Spees | 128/268 |
| 3,340,868 | 9/1967 | Darling | 128/2.06 E |
| 3,487,827 | 1/1970 | Edmark | 128/2.06 E |
| 3,518,984 | 7/1970 | Mason | 128/2.06 E |
| 3,636,922 | 1/1972 | Ketner | 128/260 X |
| 3,702,613 | 11/1972 | Panico | 128/417 |
| 3,826,245 | 7/1974 | Funfstuck | 128/2.06 E |
| 3,834,373 | 9/1974 | Sato | 128/2.06 E |
| 3,845,757 | 11/1974 | Weyer | 128/2.1 E |
| 3,989,035 | 11/1976 | Zuehlsdorff | 128/2.1 E |

*Primary Examiner*—Stephen C. Pellegrino
*Assistant Examiner*—Lee S. Cohen
*Attorney, Agent, or Firm*—A. W. Breiner

[57] ABSTRACT

A medical electrode, e.g. for electrocardiography is provided in the form of a pad, one side of which has an electrical terminal. The opposite side, which is to contact the patient's skin, has a removable assembly in which electrically conductive fluid is held in a deformable reservoir, normally a capsule, and maintained out of contact with the pad by an isolating device which yields to allow the fluid to impregnate the pad when the reservoir is pressurized. Then, on removal of the assembly, the pad is ready for use. A preferred form of isolating device has a layer of isolating material which disrupts on the pressurization and a layer of paper which is scored or otherwise arranged to localize the disruption. Using aluminum foil as the isolating material gives a very favorable satisfactory shelf-like.

12 Claims, 11 Drawing Figures

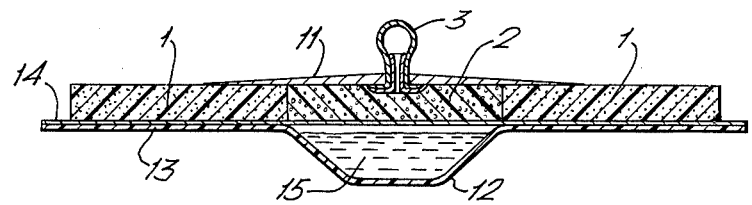
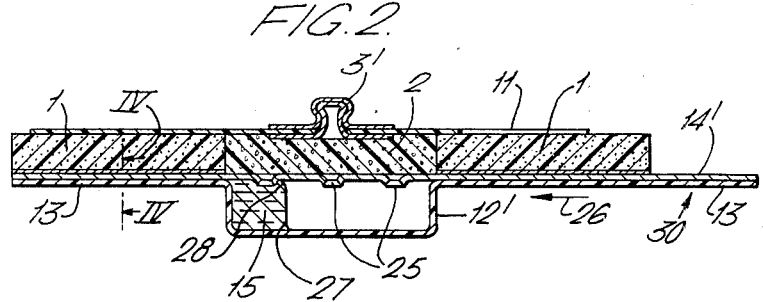
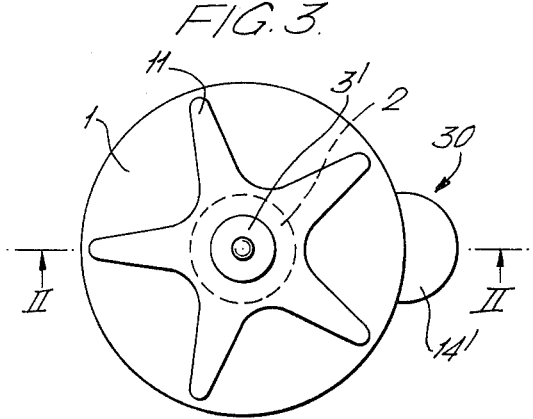
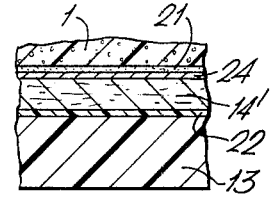

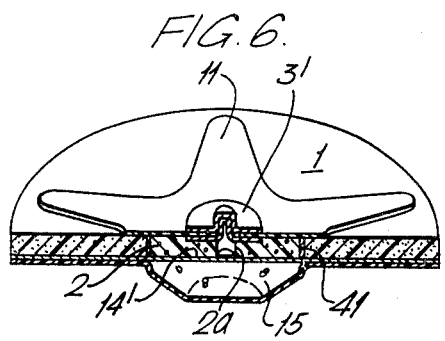
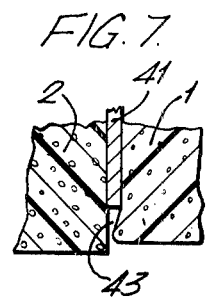
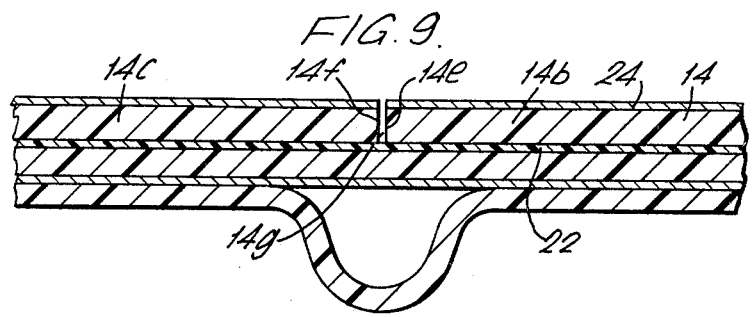
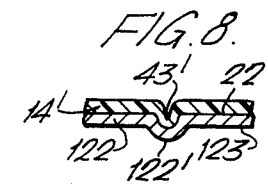
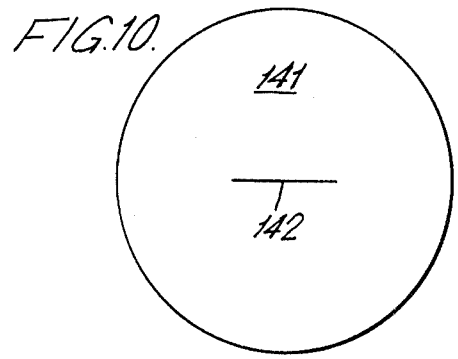
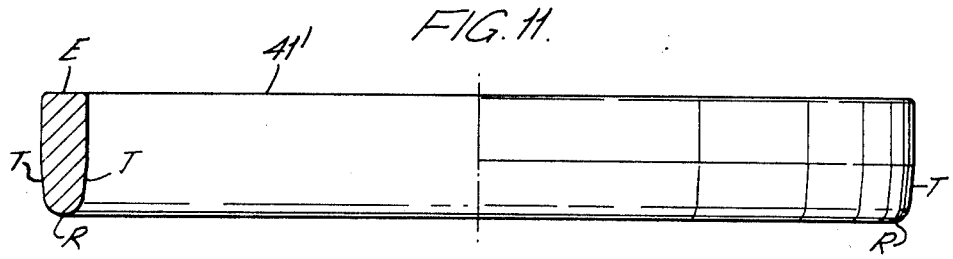

MEDICAL ELECTRODES

The present invention relates to medical apparatus and has as an object the provision of an improved form of electrode for establishing electrical communication with the skin of a patient.

Such communication is required for many purposes, a common one being for the collection of electrical signals in electro-cardiography. To provide signals which are satisfactory for normal electrocardiographs it is necessary to use electrodes moistened with an electrically conductive fluid, e.g. a saline solution or an electrically conductive fluid of an approved kind. Now that the monitoring of patients over a continuous period of several days is frequently required, much attention has been given to the provision of electrodes and conductive fluids which function reliably and without causing irritation or discomfort.

In accordance with the present invention, there is provided an electrode for establishing electrical communication with the skin of a patient which comprises a pad having, on one side thereof, a surface for contact with the skin, an electrically conductive terminal member formed of a naturally electrically conductive material and extending externally from the opposite side of said pad, a removable member mounted on said one side of the pad and covering said surface over at least a region thereof which is opposite the terminal member, a deformable reservoir mounted on the removable member and containing an electrically conductive fluid and isolating means normally isolating said fluid from said region and operable when the deformable reservoir is deformed to pressurize the fluid, to permit said fluid to flow into contact with said region, said region and said terminal member being in electrical communication at least after said flow of fluid.

The electrically conductive terminal member may, if desired, be formed of graphite but is normally formed of metal. It may be in the form of an insulated lead extending from the pad, or in the form of a connecting member for engagement with a separately provided lead or with a complementary connector on a separately provided lead. Normally, an electrocardiograph has its own leads for connection to electrodes. Since the terminal member is not exposed to the conductive fluid until the reservoir is pressurised in preparation for the use of the electrode, long-term corrosion problems are avoided. It is satisfactory, for example, to provide a nickel plated terminal member instead of the silver, or less satisfactory silver-plated, terminal members used heretofore.

In a convenient arrangement, the pad is provided on said opposite side thereof with a backing member for supporting the pad and the reservoir is deformable in the thickness direction of the pad to pressurize the fluid. The electrode can then be activated in a very convenient manner, e.g. by deforming the reservoir with the thumb whilst engaging the backing member with the fingers. It is found that especially satisfactory results are obtainable using a backing member centered about the terminal member and having a deeply radially recessed periphery. This design of the backing member gives requisite rigidity during pressurizing the reservoir and does not substantially affect the deformability of the pad, required to fit it, and maintain it comfortably fitted, to the skin of the patient, and allows the backing member to be formed of material, e.g. a synthetic resinous material of a thickness which is convenient in manufacture. A continuously curved periphery of generally sinusoidal appearance is preferred in practice.

The pad may be formed of foamed resinous material. In an especially preferred construction, the pad is formed of an apertured outer part of impermeable foamed resinous material and an inner part of foamed resinous material permeable by the electrically conductive fluid, said parts co-operating to provide said surface for contact with the skin, and said inner part providing said region of said surface. As will be understood the permeability of a foamed resinous material depends upon whether the gas phase is continuous or discontinuous.

According to a feature of the present invention, the deformable reservoir may be a capsule. Advantageously the reservoir is provided in the form of a deformable capsule part and a closure part positioned adjacent to said region of the pad, said closure part providing said isolating means.

The isolating means may be provided in the form of at least one valve. However when a closure part is provided with a deformable capsule as aforesaid, mechanical complexity is avoidable by arranging that the closure part acts to pass the fluid to the said region when the capsule is pressurized. Various arrangements are possible. In one arrangement the closure part is formed of a material which is permeable to the fluid and provided with a wax or other sealing material adapted to fail when the capsule is deformed to pressurise the fluid.

In another arrangement, the closure part is formed with perforations and no sealing material is employed. By a suitable choice of the perforation size and form, the physical properties of the fluid (eg. a gel) and of the laminar material, the mechanical properties of the capsule, and the amount of fluid employed, no significant passage of the liquid through the perforations takes place during reasonable handling and over a period of storage which is usefully long for some applications. This arrangement does however give a failure rate which is inconvenient in commercial distribution and in storage of the electrodes at the point of use.

Best results are given by providing the closure part with one or more lines of weakening, along which the material can burst when the reservoir is deformed to pressurise the fluid. Such lines of weakening may be cuts formed through part of the thickness of the closure part. A suitable arrangement using, as the closure part, a sheet of paper coated on the pad-side with an impermeable layer, e.g. of silicone wax, is to arrange the cuts so that they penetrate short of the coating layer. In this way the integrity of the isolating means does not depend materially upon the mechanical integrity of the coating layer. The cuts may be made with a press tool or roller knife. Sets of cuts having a plurality of intersections e.g. arranged in a grid-like pattern, are preferred. The reduced resistance to bursting at the intersections give a convenient arrangement.

Another suitable arrangement is to employ scored aluminium or other metallic foil, eg. aluminium foil scored by a press-knife arranged to stop short of a hard metal base. The scoring is not a pure severing action but involves plastic flow of the foil material. Typically, 15 micron aluminium is used with a press-knife which stops 7 microns short of the base.

In a most-preferred arrangement, the isolating means is formed of a first layer of a material which is impermeable to the conductive fluid and vapor exuded therefrom and is disruptable by the fluid when the fluid is pressurized and a second layer constituted to localize the disruption.

The impermeability required of the first layer is conveniently achieved by forming it of metal foil, the preferred material being aluminium foil. Chemical action between the conductive fluid and the metal foil may, in some cases, produce a non-conductive layer, but provided that the foil is not significantly affected mechanically, this can be tolerated. The electrical terminal is, of course, isolated from the conductive fluid during storage.

Complex construction of the second layer, e.g. using plastic moldings, is avoidable by forming the second layer of sheet material, conveniently paper. Localized disruptability of the first layer is obtainable by forming the sheet material with one or more apertures, one or more score lines or slits, or by forming the second layer of sections of the sheet material spaced apart to define at least one disruption zone therebetween.

For best results the first and second layers are adhesively secured together. They are most readily produced in this form from pre-formed laminated material. Using metal foil as the first (impermeable) layer and paper as the second layer, the laminated material may be scored from the paper side, leaving the metal foil impermeable but preferably weakened by embossment at the scoring. The scoring is best performed on a supply of the laminated material which is subsequently cut to form components for the electrode.

The isolating means and the gel-containing capsule or other reservoir, viz the removable member aforesaid, may in practice be provided as a sub-assembly. This sub assembly is normally attached to the pad by a layer of a tacky adhesive suitable for attachment of the pad to the patient. In manufacture, the pad may be coated with the adhesive, and the adhesive protected by a protective layer of a material which may be peeled away to prepare the pad for reception of the sub-assembly.

The pad permeable by the conductive fluid is advantageously so arranged that the region thereof which is to receive the fluid has a substantially reduced compressibility in the axial direction. With this arrangement it is found that the said region is more reliably impregnated with the fluid. Indeed if the supply of fluid is increased, as may be desirable especially for long-term monitoring purposes, the probability of the fluid spreading outwardly over the patient's skin, and thus interfering with the attachment of the electrode by adhesion, is significantly reduced so that less positive attention of the medical personnel is required.

The preferred form of the pad, as has been shown, has an impermeable outer part and a permeable inner part. The reduced compressibility is conveniently achieved by fitting an axially pressure-resistant member between the two said parts. This member may be of very simple form, e.g. a piece cut from a length of synthetic resinous tubing. For best results its axial length should be less than the thickness of the pad and it should be dimensioned and movable, or so positioned, that it does not exert undue abrasive pressure upon the skin of the patient. The nominal axial length of the piece may, it is found, be substantially less than the thickness of the pad. This is advantageous in that reliability is obtainable at readily achieved manufacturing tolerances without any exacting inspection.

As an alternative to providing a separate component, the effect may be obtained by heat-treating the outer peripheral region of the inner part or the inner peripheral region of the outer part to render the material locally more rigid by modifying the cellular structure.

The following description of preferred embodiments of an electrode provided in accordance with the invention, in which description reference is made to the accompanying drawings, is given in order to illustrate the invention.

In the drawing:

FIG. 1 shows a first embodiment in cross section,

FIG. 2 shows a second embodiment in cross section taken along line II — II of FIG. 3 which shows the embodiment in plan, FIG. 4 is a cross section taken along IV — IV of FIG. 2, FIG. 5 is an exploded perspective of a third and preferred embodiment, FIG. 6 shows half of the electrode of FIG. 5 in perspective, FIG. 7 is a cross section showing part of the electrode of FIG. 5 on an enlarged scale, FIG. 8 is a cross section showing part of the FIG. 5 electrode on an enlarged scale, FIG. 9 is a cross section showing part of an electrode according to FIG. 5 in a modified form, and FIGS. 10 and 11 show further modifications of the FIG. 5 electrode.

The electrode of FIG. 1 has an annular disc of closed-cell (impermeable) foamed polyethylene 1, the centre of which is occupied by a circular disc 2 of graphite impregnated polyurethane reticulated (and therefore permeable) foam. Embedded in disc 2 is a hollow metal terminal stud 3 formed of nickel plated brass.

Stud 3 passes through a central aperture of a backing member 11, formed of polyethylene, and having a deeply recessed peripheral shape of the form shown in FIG. 3.

Annular disc 1 and circular disc 2 together form a pad having a generally planar circular surface on the lower side as seen in FIG. 1, for contact with the skin of a patient. The properties of discs 1 and 2, and the flexibility of backing member 11, are such that the circular surface is deformable to fit the configuration of the skin at the position of application and such as to render the electrode reasonably comfortable in prolonged use.

To the circular surface is removably secured by an adhesive of medically approved dermatitic-proof type marketed by Monsanto Chemical Company Ltd., an assembly which incorporates a deformable capsule 12, vacuum-formed at the centre of a layer 13 of polyvinyl chloride, and a layer 14 of perforated paper having a coating of hydrocarbon wax. A thin layer of regenerated cellulose sheeting could be employed in place of the wax coating.

Capsule 12 contains a supply 15 of an electrolylic chloride gel. Suitable gels of medically approved type are commercially available.

To perpare the electrode for use, capsule 12 is squeezed with the thumb whilst backing member 11 is supported by the fingers. The resulting pressurization of the gel against the perforated paper causes the wax coating to fail, and allow the gel to be forced out of the capsule to contact and penetrate disc 2. Layer 14 which, as shown in FIG. 1, extends beyond the outer periphery of disc 1 is peeled away and the circular surface provided by discs 1 and 2 applied to the patient's skin where it is retained by the residual adhesive.

In this way electrical communication is established between the skin and terminal stud 3. It is not necessary for the gel to contact stud 3 before monitoring or treating a patient because of the conductivity provided by the graphite in the reticulated foam.

The electrode shown in simple to employ and, because the gel is isolated from disc 2 and terminal stud 3 before the gel is pressurized, it has a long storage life without significant corrosion problems.

Instead of the perforated end waxed material, a valve arrangement may be employed, e.g. two layers of resinous film provided with ports for the passage of gel positioned out of registry with one another, the outer layer being more deformable under the pressurization than the inner layer. Distension of the outer layer opens a passageway for the gel between the two layers and allows it to flow through the port or ports in the outer layer.

The electrode of FIGS. 2 and 3 has a pad formed by an annular disc 1 and circular disc 2 as described with reference to FIG. 1. Backing member 11 is formed of polyethylene and is secured to disc 1.

Terminal 3' is of the two-part snap fastener socket and eyelet type located by a central hole in the backing member 11 and is receivable by a complementary socket terminal (not shown) of an electrocardiograph lead.

An assembly, formed of a layer of material 14', i.e., paper, and a layer 13 of polyvinyl chloride vacuum-formed at the center to provide capsule part 12' generally cylindrical configuration, is removably adhered to the surface of disc 1, for example, by a layer of dermatitic-proof adhesive 21. Layer 14' is coated on one side with an adhesive. On its other side layer 14' is coated with a material 24 which limits the strength of adhesion by adhesive 21 (see FIG. 4).

The thicknesses of material as shown in FIGS. 2 and 4 are exaggerated where necessary for clarity of illustration.

Doubly coated layer 14' is formed at its center with an array of perforations 25. Only there perforations are shown for purposes of illustration. In practice many more perforations are provided in a regular array. Capsule part 12' is partly filled with electrolytic chloride gel 15. This gel flows slowly when the orientation of the electrode is changed. The electrode is shown in FIG. 2 with the gel in a position adopted when arrow 26 represents a vertically downward direction.

Gel 15 wets the interior of capsule part 12' (see meniscus shown at 27), but does not wet the adhesive 22 (see meniscus shown at 28) or material 24. Surface tension effects prevent penetration of the perforations 25 until capsule part 12' is sufficiently deformed by externally applied pressure. Accidental pressures applied to part 12' in transport, storage, and handling do not, in general, affect the integrity of the arrangement as the part 12' is only partially filled.

Deterioration of the gel during storage is minimal. Although the liquid component of the gel has a vapor phase which can extend through the perforations 25 into the disc 2, the closed-cellular structure of disc 1 provides a circumferential enclosure and the opposite face of disc 2 is covered by the central portion of backing member 11 as shown in FIG. 3. It is important to ensure that the peripheral recesses of backing member 11 do not extend radially inwardly to expose disc 2.

As will be apparent from FIGS. 2 and 3, the assembly 13, 14' provides a projecting tab 30 which facilitates peeling of the assembly from discs 1 and 2 after the gel has been pressed into disc 2.

The electrode of FIGS. 5 to 7 differs from that shown in FIGS. 2 to 4 in several important respects. Firstly an axially pressure-resistant member 41 is fitted between the outer circumference of disc 2 and the inner circumference of disc 1. Member 41 is cut from a length of polyethylene tubing. As shown in FIG. 7, its axial length is less than the thickness of disc 1. The capsule 121' may contain substantially more gel 15 than can the capsule 12' of the electrodes of FIGS. 1 to 4. Member 41 reduces the compressibility of disc 2. The reliability of impregnation of disc 2 with the gel is increased. Additionally, the probability of the gel spreading outwardly over the patient's skin and interfering with the attachment of the electrode by adhesion is significantly reduced. This is especially advantageous in long-term monitoring as less positive attention of the medical personnel is required.

Central aperture 2a formed in disc 2 increases the rate at which the gel can be taken-up and increases the capacity of disc 2 for the gel.

Further, as shown in FIG. 7, the disc 2 extends, at 43, above of the disc 1 to ensure positive contact with the patient. This feature is advantageously incorporated in any electrode according to the present invention.

The capsule assembly has an annular disc 24' of easy-release paper by which it is removably secured to patient-adhesive 21 applied to disc 1. Through the central aperture of disc 24' can be seen the central part of a paper layer 14' formed with a score line 43'. Layer 14' is laminated to a layer of aluminium foil 122 (FIG. 8) before score line 43' is formed and the laminate is secured by its foil layer to polyvinyl chloride layer 13 by a permanent adhesive. The foil layer is embossed and locally weakened, but left imperforate, by the scoring operation so that it provides a total seal for capsule 13' during storage. When the capsule is pressurized, the laminate disrupts along score line 43' to admit the gel to disc 2. Before pressurization, the gel 15 is sealed in the capsule by the imperforate foil to give negligible loss by evaporation during storage.

The form of the laminate and score line are shown on an enlarged scale in FIG. 8 in which the layer of adhesive laminating paper layer 14' to the foil 122 is indicated at 22. A layer of adhesive for laminating the foil to the capsule is applied at 123. The paper layer 14' is stretched at the score line 43' and weakened by localized compression, localized stretching, and general reorganisation of the fibrous structure. Partial cutting of the paper may be involved in some cases in addition to pure scoring. Score lines are used extensively in the packaging art, e.g. to promote folding of paper or cardboard at a required position. The principles are accordingly widely understood.

During the scoring operation the foil is deformed at region 122' to give the visual appearance of a sharp crease line.

Capsule 12' may be sufficiently filled with the gel 15 to ensure that no great manual effort is required to disrupt the foil. Desirably some air space is left within the capsule to provide some elasticity and thereby ensure that minor deformations caused by rough handling do not disrupt the foil.

The embodiment of FIG. 9 is similar to that of FIG. 5 except in that the scored paper layer 14' is replaced by two separate sections of paper 14b and 14c having opposed straight edges 14e and 14f. A narrow gap 14g is shown between these edges in FIG. 12 but, in practice, no gap is necessary if the adhesive 22 does not penetrate between the opposed edges.

As an alternative to using two sections of paper as in FIG. 9, there may be employed a paper disc 141 shown in FIG. 10 formed, when it is to cover the capsule, with a slit 142.

FIG. 11 shows, partly in elevation and partly in cross section a form of pressure resistant member 41' which has been found to be preferable to the member 41 of FIG. 5. Ring 41' is tapered at 10° inside and out over part of its axial length at T. The end which is to face the patient is rounded at R as shown. In this way, relative movements between the ring, the inner disc 2 and the outer disc 1 are facilitated and spread of gel over disc 1 is the better imposed.

End E is formed flat to mate with backing member 11, and is advantageously secured thereto by an adhesive or by welding.

An electrode as described with reference to the drawings is normally produced by mating two sub-assemblies, i.e. one comprising the electrical terminal, backing member 11 and discs 1 and 2, usually with a member 41 or 41' and the other comprising the gel-containing molding and the cover therefor. Joining the parts of the sub-assemblies is conveniently effected using heat activated adhesives and radio frequency heating applied using electrodes formed and mounted to clamp the parts together under mechanical pressure.

It will be appreciated that the foregoing description is given by way of illustration only and that various departures may be made therefrom, by those skilled in the art, without departing from the spirit and scope of the invention.

I claim:

1. An electrode for establishing electrical communication with the skin of a patient, said electrode comprising a pad in the form of an inner pad part of fluid permeable material and, surrounding the inner pad part, an outer pad part of fluid impermeable material, said pad parts together providing a composite face for securing the pad to the skin and an outer face opposite said composite face, a backing member secured to said outer face and wholly covering the inner pad part on said outer face and extending outwardly to cover the outer pad part on said outer face over a region surrounding the inner pad part, an electrically conductive terminal member formed of a naturally electrically conductive material extending through the backing member and contacting the inner pad part, a layer of tacky adhesive covering the outer pad part at the composite face, and a capsule assembly having a deformable reservoir part, a supply of electrically conductive liquid within the reservoir part, said liquid partially filling the reservoir part to leave a gas space therein, an integral flange part surrounding said reservoir part, and a closure part laminated to the flange part and extending over the surrounded reservoir part to seal the liquid therein, said closure part being secured to the outer pad part by said adhesive with the flange part facing the outer pad part of the composite face and the reservoir part facing the inner pad part of the composite face, said closure part being formed of two layers laminated together, the first layer facing inwardly into the reservoir part and being formed of a material which is impermeable to the conductive liquid and vapors evolved therefrom but is sufficiently weak to disrupt under pressure, and permit the electrically conductive liquid to flow into and impregnate the inner pad part on manual deformation of the reservoir part, and the second layer facing the inner pad part and serving to strengthen the layer facing inwardly into the reservoir part and being provided with at least one weakening formation to localize and control said disruption.

2. An electrode according to claim 1 in which the electrically conductive material is a metal.

3. An electrode according to claim 1 in which the formation is a slit.

4. An electrode according to claim 1 in which the formation is a gap.

5. An electrode according to claim 1 in which the formation is a scoring.

6. An electrode according to claim 5 in which the second layer is imperforate at the scoring.

7. An electrode according to claim 1 in which the second layer is formed of paper.

8. An electrode according to claim 1 in which the first layer is formed of metal foil.

9. An electrode according to claim 1 in which the first layer is formed by aluminum foil.

10. an electrode according to claim 1 having an axially pressure-resistant member located between the outer pad part and the inner pad part.

11. An electrode according to claim 10 in which the pressure-resistant member is a piece of tubular material.

12. An electrode according to claim 1 having an annular disc of easy release paper positioned between the closure part and the adhesive.

* * * * *